(12) United States Patent
Lightner et al.

(10) Patent No.: US 7,750,205 B2
(45) Date of Patent: Jul. 6, 2010

(54) GENERATION OF PLANTS WITH ALTERED OIL CONTENT

(75) Inventors: Jonathan Lightner, Johnston, IA (US); Stephanie K. Clendennen, Kingsport, TN (US)

(73) Assignee: Agrinomics, LLC, Portland, OR (US)

( * ) Notice: Subject to any disclaimer, the term of this patent is extended or adjusted under 35 U.S.C. 154(b) by 501 days.

(21) Appl. No.: 10/539,488

(22) PCT Filed: Dec. 18, 2003

(86) PCT No.: PCT/US03/40992

§ 371 (c)(1),
(2), (4) Date: Mar. 13, 2006

(87) PCT Pub. No.: WO2004/056969

PCT Pub. Date: Jul. 8, 2004

(65) Prior Publication Data

US 2006/0168686 A1    Jul. 27, 2006

Related U.S. Application Data

(60) Provisional application No. 60/434,795, filed on Dec. 18, 2002.

(51) Int. Cl.
   *C12N 15/82* (2006.01)
(52) U.S. Cl. .................................................. 800/281
(58) Field of Classification Search ...................... None
   See application file for complete search history.

(56) References Cited

U.S. PATENT DOCUMENTS

| | | | |
|---|---|---|---|
| 5,500,361 A | 3/1996 | Kinney | |
| 5,639,790 A | 6/1997 | Voelker et al. | |
| 5,704,160 A | 1/1998 | Bergquist et al. | |
| 6,184,355 B1 | 2/2001 | James et al. | |
| 6,229,033 B1 | 5/2001 | Knowlton | |
| 6,248,939 B1 | 6/2001 | Leto et al. | |
| 6,307,128 B1 | 10/2001 | Jaworski et al. | |
| 6,348,642 B1 | 2/2002 | Knauf et al. | |

FOREIGN PATENT DOCUMENTS

| WO | WO98/54954 | 12/1998 |
|---|---|---|
| WO | WO 99/67367 | 12/1999 |
| WO | WO01/83697 | 11/2001 |

OTHER PUBLICATIONS

Katavic et al., "Utility of the *Arabidopsis FAE1* and yeast *SLC-1* genes for improvements in erucic acid and oil content in rapeseed," *Biochemical Society Transactions*, 28(6):935-937, 2000.
Anoop et al., "Modulation of citrate metabolism alters aluminum tolerance in yeast and transgenic canola overexpressing a mitochondrial citrate synthase," *Plant Physiol.*, 132:2205-2217, 2003.
Beisson et al., "Arabidopsis genes involved in acyl lipid metabolism. A 2003 census of the candidates, a study of the distribution of expressed sequence tags in organs, and a web-based database," *Plant Physiol.*, 132:681-697, 2003.
Bert et al., "Comparative genetic analysis of quantitative traits in sunflower (*Helianthus annuus* L.). 2. Characterisation of QTL involved in developmental and agronomic traits," *Theor. Appl. Genet.*, 107:181-189, 2003.
Colbert et al., "High-throughput screening for induced point mutations," *Plant Physiol.*, 126(2):480-484, 2001.
Dehesh et al., "Overexpression of 3-ketoacyl-acyl-carrier protein synthase IIIs in plants reduces the rate of lipid synthesis," *Plant Physiol.*, 125:1103-1114, 2001.
Eastmond and Graham, "Re-examining the role of glyoxylate cycle in oilseeds," *Trends Plant Sci.*, 6(2):72-77, 2001.
Eccleston and Ohlrogge, "Expressions of lauroyl-acyl carrier protein thioesterase in *brassica napus* seeds induces pathways for both fatty acid oxidation and biosynthesis and implies a set point for triacylglycerol accumulation," *Plant Cell.* 10:613-621, 1998.
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in Arabidopsis," *Plant Cell*, 17:182-203, 2005.
Feldmann et al., "A Dwarf Mutant of Arabidopsis Generated by T-DNA Insertion Mutagenesis," *Science*, 243(4896):1351-1354, 1989.
Focks and Benning, "*wrinkled1*: A novel, low-seed-oil mutant of Arabidopsis with a deficiency in the seed-specific regulation of carbohydrate metabolism," *Plant Physiol.*, 118:91-101, 1998.
Girke et al., "Microarray analysis of developing Arabidopsis seeds," *Plant Physiol.*, 124:1570-1581, 2000.
Han et al., "Functional characterization of β-ketoacyl-CoA synthase genes from *Brassica napus* L.," *Plant Molecular Biology*, 46:229-239, 2001.
Jako et al., "Seed-specific over-expression of an Arabidopsis cDNA encoding a diacylglycerol acyltransferase enhances seed oil content and seed weight," *Plant Physiol.*, 126(2):861-874, 2001.
James and Dooner, "Isolation of EMS-induced mutants in Arabidopsis altered in seed fatty acid composition," *Theor. Appl. Genet.*, 80(2):241-245, 1990.
James et al., "Directed Tagging of the Arabidopsis FATTY ACID ELONGATION1 (FAE1) Gene with the Maize Transposon Activator," *Plant Cell*, 7:309:319, 1995.
Katavic et al., "Alteration of seed fatty acid composition by an ethyl methanesulfonate-induced mutation in Arabidopsis thaliana affecting diacylglycerol acyltransferase activity," *Plant Physiol.*, 108:399-409, 1995.
Larson et al., "Acyl CoA profiles of transgenic plants that accumulate medium-chain fatty acids indicate inefficient storage lipid synthesis in developing oilseeds," *Plant J.*, 32:519-527, 2002.

(Continued)

*Primary Examiner*—Elizabeth F McElwain
(74) *Attorney, Agent, or Firm*—Klarquist Sparkman, LLP

(57) ABSTRACT

The present invention is directed to plants that display an altered oil content phenotype due to altered expression of a HIO102 nucleic acid. The invention is further directed to methods of generating plants with an altered oil content phenotype.

4 Claims, No Drawings

OTHER PUBLICATIONS

Lassner et al., "A Jojoba β-Ketoacyl-CoA Synthase cDNA Complements the Canola Fatty Acid Elongation Mutation in Transgenic Plants," *Plant Cell*, 8:281-292, 1996.

Lemieux et al., "Mutants of Arabidopsis with alterations in seed lipid fatty acid composition," *Theor. Appl. Genet.*, 80(2):234-240, 1990.

Lin et al., "The Pex16p homolog SSE1 and storage organelle formation in *Arabidopsis* seeds," Science. 284:328-330, 1999.

Lionneton et al., "Development of an AFLP-based linkage map and localization of QTLs for seed fatty acid content in condiment mustard (Brassica juncea)," *Genome*, 45(6):1203-1215, 2002.

Liu and Butow, "A transcriptional switch in the expression of yeast tricarboxylic acid cycle genes in response to a reduction or loss of respiratory function," *Mol. Cell. Biol.*, 19:6720-6728, 1999.

McCallum et al., "Targeted screening for induced mutations," *Nat. Biotechnol.*, 18(4):455-457, 2000.

Mekhedov et al., "Toward a functional catalog of the plant genome. A survey of genes for lipid biosynthesis," *Plant Physiol.*, 122:389-401, 2000.

Moire et al., "Impact of unusual fatty acid synthesis on futile cycling through β-oxidation and on gene expression in transgenic plants," *Plant Physiol.*, 134:432-442, 2004.

Neuhaus and Emes, "Nonphotosynthetic Metabolism in Plastids," *Annu. Rev. Plant Physiol. Plant Mol. Biol.*, 51:111-140, 2000.

O'Hara et al., "Fatty acid and lipid biosynthetic genes are expressed at constant molar ratios but different absolute levels during embryogenesis," *Plant Physiol.*, 129:310-320, 2002.

Okuley et al., "Arabidopsis FAD2 Gene Encodes the Enzyme That Is Essential for Polyunsaturated Lipid Synthesis," *Plant Cell*, 6:147-158, 1994.

Pritchard et al., "Germination and storage reserve mobilization are regulated independently in *Arabidopsis* ," *Plant J.*, 31(5):639-647, 2002.

Rangasamy and Ratledge, "Compartmentation of ATP:Citrate lyase in plants," *Plant Physiol.*, 122:1225-1230, 2000.

Rangasamy and Ratledge, "Genetic enhancement of fatty acid synthesis by targeting rat liver ATP:citrate lyase into plastids of tobacco," *Plant Physiol.*, 122:1231-1238, 2000.

Ratledge et al, "Correlation of ATP/citrate lyase activity with lipid accumulation in developing seeds of *Brassica napus* L.," *Lipids*, 32(1):7-12, 1997.

Rawsthorne, S., "Carbon flux and fatty acid synthesis in plants," *Prog Lipid Res.*, 41:182-196, 2002.

Ruuska et al., "Contrapuntal networks of gene expression during Arabidopsis seed filling," *Plant Cell*, 14:1191-1206, 2002.

Rylott et al., "Co-ordinate regulation of genes involved in storage lipid mobilization in *Arabidopsis thaliana*," *Biochem Soc. Trans.*, 29:283-287, 2001.

Schnarrenberger and Martin, "Evolution of the enzymes of the citric acid cycle and the glyoxylate cycle of higher plants, A case study of endosymbiotic gene transfer," *Eur. J. Biochem.*, 269:868-883, 2002.

Schnurr et al., "Characterization of an acyl-CoA synthetase from *Arabidopsis thaliana*," *Biochem Soc. Trans.*, 28(6):957-958, 2000.

Shockey et al., "Characterization of the AMP-binding protein gene family in *Arabidopsis thaliana*: will the real acyl-CoA synthetases please stand up?" *Biochem. Soc. Trans.*, 28(6):955-957, 2000.

Thelen et al., "Biotin carboxyl carrier protein isoforms in Brassicaceae oilseeds," *Biochem. Soc. Trans.*, 28(6):595-598, 2000.

Wada et al., "Role of a positive regulator of root hair development, CAPRICE, in Arabidopsis root epidermal cell differentiation," *Development*, 129(23):5409-5419, 2002.

White et al., "A new set of Arabidopsis expressed sequence tags from developing seeds. The metabolic pathway from carbohydrates to seed oil," *Plant Physiol.*, 124:1582-1594, 2000.

Yadav et al., "Cloning of higher plant omega-3 fatty acid desaturases," *Plant Physiol.*, 103(2):467-476, 1993.

Comai et al., "Efficient discovery of DNA polymorphisms in natural populations by Ecotilling," *The Plant Journal*, 37:778-786 (2004).

GENERATION OF PLANTS WITH ALTERED OIL CONTENT

REFERENCE TO RELATED APPLICATIONS

This is the §371 U.S. National Stage of International Application No. PCT/US2003/040992, filed on Dec. 18, 2003, which was published in English under PCT Article 21(2), and which in turn claims the benefit of U.S. provisional patent application No. 60/434,795 filed Dec. 18, 2002, both of which are hereby incorporated by reference.

BACKGROUND OF THE INVENTION

The ability to manipulate the composition of crop seeds, particularly the content and composition of seed oils, has important applications in the agricultural industries, relating both to processed food oils and to oils for animal feeding. Seeds of agricultural crops contain a variety of valuable constituents, including oil, protein and starch. Industrial processing can separate some or all of these constituents for individual sale in specific applications. For instance, nearly 60% of the US soybean crop is crushed by the soy processing industry. Soy processing yields purified oil, which is sold at high value, while the remainder is sold principally for lower value livestock feed (US Soybean Board, 2001 Soy Stats). Canola seed is crushed to produce oil and the co-product canola meal (Canola Council of Canada). Nearly 20% of the 1999/2000 US corn crop was industrially refined, primarily for production of starch, ethanol and oil (Corn Refiners Association). Thus, it is often desirable to maximize oil content of seeds. For instance, for processed oilseeds such as soy and canola, increasing the absolute oil content of the seed will increase the value of such grains. For processed corn it may be desired to either increase or decrease oil content, depending on utilization of other major constituents. Decreasing oil may improve the quality of isolated starch by reducing undesired flavors associated with oil oxidation. Alternatively, in ethanol production, where flavor is unimportant, increasing oil content may increase overall value. In many fed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors.

Biotechnological manipulation of oils can provide compositional alteration and improvement of oil yield. Compositional alterations include high oleic soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from ~3.5% to ~7%, improving the energy content of the grain.

While it has been fruitful, the HOC production system has inherent limitations. First, the system of having a low percentage of pollinators responsible for an entire field's seed set contains inherent risks, particularly in drought years. Second, oil contents in current HOC fields have plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

The most obvious target crops for the processed oil market are soy and rapeseed, and a large body of commercial work (e.g., U.S. Pat. No. 5,952,544; PCT application WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (axmieux B, et al. 1990, Theor Appl Genet 80, 234-240; James D W and Dooner H K (1990) Theor Appl Genet 80, 241-245). T-DNA mutagenesis screens (Feldmann et al., *Science* 243: 1351-1354, 1989) that detected altered fatty acid composition identified the omega 3 desaturase (FAD3) and delta-12 desaturase (FAD2) genes (U.S. Pat. No. 5,952,544; Yadav N S et al. (1993) Plant Physiol 103, 467-476; Okuley et al., Plant Cell. 1994 January;6(1):147-58). A screen which focused on oil content rather than oil quality, analyzed chemically-induced mutants for wrinkled seeds or altered seed density, from which altered seed oil content was inferred (Focks N and Benning C, Plant Physiol 118:91-101, 1998). Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al, Plant Physiol. 1995 May; 108(1):399-409). It was further shown that seed-specific over-expression of the DGAT cDNA was associated with increased seed oil content (Jako et al., Plant Physiol. 2001 June;126(2):861-74).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., Science (1992) 258: 1350-1353; Weigel et al., Plant Physiology (2000) 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., Plant Cell (1996) 8:659-671, Schaffer et al., Cell (1998) 93: 1219-1229; Pridborg et al., Plant Cell (1999)11: 1019-1032; Kardailsky et al., Science (1999) 286:1962-1965); Christensen S et al., $9^{th}$ International Conference on *Arabidopsis* Research. Univ. of Wisconsin-Madison, Jun. 2428, 1998. Abstract 165).

SUMMARY OF THE INVENTION

The invention provides a transgenic plant having a high oil phenotype. The transgenic plant comprises a transformation vector comprising a nucleotide sequence that encodes or is complementary to a sequence that encodes a HIO102 polypeptide. In preferred embodiments, the transgenic plant is selected from the group consisting of rapeseed, soy, corn, sunflower, cotton, cocoa, safflower, oil palm, coconut palm, flax, castor and peanut. The invention further provides a method of producing oil comprising growing the transgenic plant and recovering oil from said plant.

The transgenic plant of the invention is produced by a method that comprises introducing into progenitor cells of the plant a plant transformation vector comprising a nucleotide sequence that encodes or is complementary to a sequence that encodes a HIO0102 polypeptide, and growing the transformed progenitor cells to produce a transgenic plant, wherein the HIO102 polynucleotide sequence is expressed causing the high oil phenotype.

DETAILED DESCRIPTION OF THE INVENTION

DEFINITIONS

Unless otherwise indicated, all technical and scientific terms used herein have the same meaning as they would to one skilled in the art of the present invention. Practitioners are particularly directed to Sambrook et al. Molecular Cloning: A Laboratory Manual (Second Edition), Cold Spring Harbor Press, Plainview, N.Y.,1989, and Ausubel F M et al. Current Protocols in Molecular Biology, John Wiley & Sons, New York, N.Y., 1993, for definitions and terms of the art. It is to be understood that this invention is not limited to the particular methodology, protocols, and reagents described, as these may vary.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, propagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "altered oil content phenotype" refers to measurable phenotype of a genetically modified plant, where the plant displays a statistically significant increase or decrease in overall oil content (i.e., the percentage of seed mass that is oil), as compared to the similar, but non-modified plant. A high oil phenotype refers to an increase in overall oil content.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic.

Identification of Plants with an Altered Oil Content Phenotype

We used an *Arabidopsis* activation tagging screen to identify the association between the gene we have designated "HIO102," (At4g34250; GI#18418411:1-1482 encoding a fatty acid elongase-like protein (GI#15235309), and an altered oil content phenotype (specifically, a high oil phenotype). Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al, supra). When the T-DNA inserts into the genome of transformed plants, the enhancer element can cause up-regulation genes in the vicinity, generally within about 10 kilobase (kb) of the insertion. T1 plants were exposed to the selective agent in order to specifically recover transformed plants that expressed the selectable marker and therefore harbored T-DNA insertions. Samples of approximately 15-20 T2 seeds were collected from transformed T1 plants, and lipids were extracted from whole seeds. Gas chromatography (GC) analysis was performed to determine fatty acid content and composition of seed samples.

An *Arabidopsis* line that showed a high-oil phenotype was identified, wherein oils (i.e., fatty acids) constituted approximately 35% of seed mass. The association of the HIO102 gene with the high oil phenotype was discovered by analysis of the genomic DNA sequence flanking the T-DNA insertion in the identified line. Accordingly, HIO102 genes and/or polypeptides may be employed in the development of genetically modified plants having a modified oil content phenotype ("a HIO102 phenotype"). HIO102 genes may be used in the generation of oilseed crops that provide improved oil yield from oilseed processing and in the generation of feed grain crops that provide increased energy for animal feeding. HIO102 genes may further be used to increase the oil content of specialty oil crops, in order to augment yield of desired unusual fatty acids. Transgenic plants that have been genetically modified to express HIO102 can be used in the production of oil, wherein the transgenic plants are grown, and oil is obtained from plant parts (e.g. seed) using standard methods.

HIO102 Nucleic Acids and Polypeptides

*Arabidopsis* HIO102 nucleic acid (genomic DNA) sequence is provided in SEQ ID NO:1 and in Genbank entry GI#18418411:1-1482. The corresponding protein sequence is provided in SEQ ID NO:2 and in GI#15235309. Nucleic acids and/or proteins that are orthologs or paralogs of *Arabidopsis* HIO102, are described in Example 3 below.

As used herein, the term "HIO102 polypeptide" refers to a full-length HIO102 protein or a fragment, derivative (variant), or ortholog thereof that is "functionally active," meaning that the protein fragment, derivative, or ortholog exhibits one or more or the functional activities associated with the polypeptide of SEQ ID NO:2. In one preferred embodiment, a functionally active HIO102 polypeptide causes an altered oil content phenotype when mis-expressed in a plant. In a further preferred embodiment, mis-expression of the HIO102 polypeptide causes a high oil phenotype in a plant. In another embodiment, a functionally active HIO102 polypeptide is capable of rescuing defective (including deficient) endogenous HIO102 activity when expressed in a plant or in plant cells; the rescuing polypeptide may be from the same or from a different species as that with defective activity. In another embodiment, a functionally active fragment of a full length HIO102 polypeptide (i.e., a native polypeptide having the sequence of SEQ ID NO:2 or a naturally occurring ortholog thereof) retains one of more of the biological properties associated with the full-length HIO102 polypeptide, such as signaling activity, binding activity, catalytic activity, or cellular or extra-cellular localizing activity. A HIO102 fragment preferably comprises a HIO102 domain, such as a C- or N-terminal or catalytic domain, among others, and preferably comprises at least 10, preferably at least 20, more preferably at least 25, and most preferably at least 50 contiguous amino acids of a HIO102 protein. Functional domains can be identified using the PFAM program (Bateman A et al., 1999 Nucleic Acids Res 27:260-262; website at pfam.wustl.edu). A preferred HIO102 fragment comprises Chalcone and stilbene synthases, C-terminal domain (PF02797). Functionally active variants of full-length HIO102 polypeptides or fragments thereof include polypeptides with amino acid insertions, deletions, or substitutions that retain one of more of the biological properties associated with the full-length HIO102 polypeptide. In some cases, variants are generated that change the post-translational processing of a HIO102 polypeptide. For instance, variants may have altered protein transport or protein localization characteristics or altered protein half-life compared to the native polypeptide.

As used herein, the term "HIO102 nucleic acid" encompasses nucleic acids with the sequence provided in or complementary to the sequence provided in SEQ ID NO:1, as well as functionally active fragments, derivatives, or orthologs thereof. A HIO102 nucleic acid of this invention may be DNA, derived from genomic DNA or cDNA, or RNA.

In one embodiment, a functionally active HIO102 nucleic acid encodes or is complementary to a nucleic acid that encodes a functionally active HIO102 polypeptide. Included within this definition is genomic DNA that serves as a template for a primary RNA transcript (i.e., an mRNA precursor) that requires processing, such as splicing, before encoding the functionally active HIO102 polypeptide. A HIO102 nucleic acid can include other non-coding sequences, which may or may not be transcribed; such sequences include 5' and 3'

UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO102 polypeptide, or an intermediate form. A HIO102 polynucleotide can also include heterologous coding sequences, for example, sequences that encode a marker included to facilitate the purification of the fused polypeptide, or a transformation marker.

In another embodiment, a functionally active HIO102 nucleic acid is capable of being used in the generation of loss-of-function HIO102 phenotypes, for instance, via antisense suppression, co-suppression, etc.

In one preferred embodiment, a HIO102 nucleic acid used in the methods of this invention comprises a nucleic acid sequence that encodes or is complementary to a sequence that encodes a HIO102 polypeptide having at least 50%, 60%, 70%, 75%, 80%, 85%, 90%, 95% or more sequence identity to the polypeptide sequence presented in SEQ ID NO:2.

In another embodiment a HIO102 polypeptide of the invention comprises a polypeptide sequence with at least 50% or 60% identity to the HIO102 polypeptide sequence of SEQ ID NO:2, and may have at least 70%, 80%, 85%, 90% or 95% or more sequence identity to the HIO102 polypeptide sequence of SEQ ID NO:2. In another embodiment, a HIO102 polypeptide comprises a polypeptide sequence with at least 50%, 60%, 70%, 80%, 85%, 90% or 95% or more sequence identity to a functionally active fragment of the polypeptide presented in SEQ ID NO:2, such as Chalcone and stilbene synthases, C-terminal domain. In yet another embodiment, a HIO102 polypeptide comprises a polypeptide sequence with at least 50%, 60%, 70%, 80%, or 90% identity to the polypeptide sequence of SEQ ID NO:2 over its entire length and comprises a Chalcone and stilbene synthases, C-terminal domain.

In another aspect, a HIO102 polynucleotide sequence is at least 50% to 60% identical over its entire length to the HIO102 nucleic acid sequence presented as SEQ ID NO:1, or nucleic acid sequences that are complementary to such a HIO102 sequence, and may comprise at least 70%, 80%, 85%, 90% or 95% or more sequence identity to the HIO102 sequence presented as SEQ ID NO:1 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410; website at blast.wustl.edu/blast/README.html) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the nucleic acid sequence of SEQ ID NO:1. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of SEQ ID NO:1 under stringent hybridization conditions that are: prehybridization of filters containing nucleic acid for 8 hours to overnight at 65° C. in a solution comprising 6× single strength citrate (SSC) (1× SSC is 0.15 M NaCl, 0.015 M Na citrate; pH 7.0), 5× Denhardt's solution, 0.05% sodium pyrophosphate and 100 μg/ml herring sperm DNA; hybridization for 18-20 hours at 65° C. in a solution containing 6× SSC, 1× Denhardt's solution, 100 μg/ml yeast tRNA and 0.05% sodium pyrophosphate; and washing of filters at 65° C. for 1 h in a solution containing 0.1× SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5× SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18-20 h at 40° C. in a solution containing 35% fornmaride, 5× SSC, 50 mM Tris-HCl (pH 7.5), 5 mM EDTA, 0.02% PVP, 0.02% Ficoll, 0.2% BSA, 100 μg/ml sallnon sperm DNA, and 10% (wt/vol) dextran sulfate; followed by washing twice for 1 hour at 55° C. in a solution containing 2× SSC and 0.1% SDS. Alternatively, low stringency conditions can be used that comprise: incubation for 8 hours to overnight at 37° C. in a solution comprising 20% formnamide, 5× SSC, 50 mM sodium phosphate (pH 7.6), 5× Denhardt's solution, 10% dextran sulfate, and 20 μg/ml denatured sheared salmon sperm DNA; hybridization in the same buffer for 18 to 20 hours; and washing of filters in 1× SSC at about 37° C. for 1 hour.

As a result of the degeneracy of the genetic code, a number of polynucleotide sequences encoding a HIO102 polypeptide can be produced. For example, codons may be selected to increase the rate at which expression of the polypeptide occurs in a particular host species, in accordance with the optimum codon usage dictated by the particular host organism (see, e.g., Nakamura et al, 1999, Nucleic Acids Res 27:292). Such sequence variants may be used in the methods of this invention.

The methods of the invention may use orthologs of the *Arabidopsis* HIO102. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, supra; Dieffenbach C and Dveksler G (Eds.) PCR Primer: A Laboratory Manual, Cold Spring Harbor Laboratory Press, NY, 1989). For instance, methods for generating a cDNA library from the plant species of interest and probing the library with partially homologous gene probes are described in Sambrook et al, supra. A highly conserved portion of the *Arabidopsis* HIO102 coding sequence may be used as a probe. HIO102 ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known HIO102 polypeptides are used for ortholog isolation (see, e.g., Harlow E and Lane D, Using Antibodies: A Laboratory Manual, Cold Spring Harbor Laboratory Press, 1999, New York). Western blot analysis can determine that a HIO102 ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., supra. Once the candidate ortholog(s) are identified by any of these means, candidate orthologous sequence are used as bait (the "query") for the reverse BLAST against sequences from *Arabidopsis* or other species in which HIO102 nucleic acid and/or polypeptide sequences have been identified.

HIO102 nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel TA et al., Methods Enzymol. 204:125-39, 1991), may be used to introduce desired changes into a cloned nucleic acid.

In general, the methods of the invention involve incorporating the desired form of the HIO102 nucleic acid into a plant expression vector for transformation of in plant cells, and the HIO102 polypeptide is expressed in the host plant.

An isolated HIO102 nucleic acid molecule is other than in the form or setting in which it is found in nature and is identified and separated from least one contaminant nucleic acid molecule with which it is ordinarily associated in the natural source of the HIO102 nucleic acid. However, an isolated HIO102 nucleic acid molecule includes HIO102 nucleic acid molecules contained in cells that ordinarily express HIO102 where, for example, the nucleic acid molecule is in a chromosomal location different from that of natural cells.

Generation of Genetically Modified Plants with an Altered Oil Content Phenotype

HIO102 nucleic acids and polypeptides may be used in the generation of genetically modified plants having a modified oil content phenotype. As used herein, a "modified oil content phenotype" may refer to modified oil content in any part of the plant; the modified oil content is often observed in seeds. In a preferred embodiment, altered expression of the HIO102 gene in a plant is used to generate plants with a high oil phenotype.

The methods described herein are generally applicable to all plants. Although activation tagging and gene identification is carried out in *Arabidopsis*, the HIO102 gene (or an ortholog, variant or fragment thereof) may be expressed in any type of plant. In a preferred embodiment, the invention is directed to oil-producing plants, which produce and store triacylglycerol in specific organs, primarily in seeds. Such species include soybean (*Glycine max*), rapeseed and canola (including *Brassica napus, B. campestris*), sunflower (*Helianthus anizus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus commuizis*) and peanut (*Arachis hypogaea*). The invention may also be directed to fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species that may be a source of unique fatty acids.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to Agrobacterium-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an HIO102 polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.).

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as rapeseed se Block et al., Plant Physiol. (1989) 91:694-701), sunflower (Everett et al., Bio/Technology (1987) 5:1201), and soybean (Christou et al., Proc. Natl. Acad. Sci USA (1989) 86:7500-7504; Kline et al., Nature (1987) 327:70).

Expression (including transcription and translation) of HIO102 may be regulated with respect to the level of expression, the tissue type(s) where expression takes place and/or developmental stage of expression. A number of heterologous regulatory sequences (e.g., promoters and enhancers) are available for controlling the expression of a HIO102 nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the 35S CaMV (Jones J D et al, Transgenic Res 1:285-297 1992), the CsVMV promoter (Verdaguer B et al., Plant Mol Biol 37:1055-1067, 1998) and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., Plant Mol Bio 21:625-640, 1993).

In one preferred embodiment, HIO102 expression is under control of regulatory sequences from genes whose expression is associated with early seed and/or embryo development. Legume genes whose promoters are associated with early seed and embryo development include *V. faba legumin* (Baumlein et al., 1991, Mol Gen Genet 225:121-8; Baumlein et al., 1992, Plant J 2:233-9), *V. faba usp* (Fiedler et al., 1993, Plant Mol Biol 22:669-79), pea *convicilin* (Bown et al., 1988, Biochem J 251:717-26), pea *lectin* (dePater et al., 1993, Plant Cell 5:877-86), *P. vulgaris beta phaseolin* (Bustos et al., 1991, EMBO J 10: 1469-79), *P. vulgaris* DLEC2 and PHS [beta] (Bobb et al, 1997, Nucleic Acids Res 25:641-7), and soybean beta-Conglycinin, 7S storage protein (Chamberland et al., 1992, Plant Mol Biol 19:937-49). Cereal genes whose promoters are associated with early seed and embryo development include rice glutelin ("GluA-3," Yoshihara and Takaiwa, 1996, Plant Cell Physiol 37:107-11; "GluB-1," Takaiwa et al., 1996, Plant Mol Biol 30:1207-21; Washida et al., 1999, Plant Mol Biol 40:1-12; "Gt3," Leisy et al., 1990, Plant Mol Biol 14:41-50), rice *prolamin* (Zhou & Fan, 1993, Transgenic Res 2:141-6), wheat *prolamin* (Hammond-Kosack et al., 1993, EMBO J 12:545-54), maize *zein* (Z4, Matzke et al., 1990, Plant Mol Biol 14:323-32), and barley B-hordeins (Entwistle et al., 1991, Plant Mol Biol 17:1217-31). Other genes whose promoters are associated with early seed and embryo development include oil palm GLO7A (7S globulin, Morcillo et al., 2001, Physiol Plant 112:233-243), *Brassica napus napin*, 2S storage protein, and napA gene (Josefsson et al., 1987, J Biol Chem 262:12196-201; Stalberg et al., 1993, Plant Mol Biol 1993 23:671-83; Ellerstrom et al., 1996, Plant Mol Biol 32:1019-27), *Brassica napus oleosin* (Keddie et al., 1994, Plant Mol Biol 24:327-40), *Arabidopsis oleosin* (Plant et al., 1994, Plant Mol Biol 25:193-205), *Arabidopsis* FAE1 (Rossak et al., 2001, Plant Mol Biol 46:717-25), *Canavalia gladiata* conA (Yamamoto et al., 1995, Plant Mol Biol 27:729-41), and *Catharanthus roseus* strictosidine synthase (Str, Ouwerkerk and Memelink, 1999, Mol Gen Genet 261:635-43). In another preferred embodiment, regulatory sequences from genes expressed during oil biosynthesis are used (see, e.g., U.S. Pat. No. 5,952,544). Alternative promoters are from plant storage protein genes (Bevan et al, 1993, Philos Trans R Soc Lond B Biol Sci 342:209-15).

In yet another aspect, in some cases it may be desirable to inhibit the expression of endogenous HIO102 in a host cell. Exemplary methods for practicing this aspect of the invention include, but are not limited to antisense suppression (Smith, et al., Nature 334:724-726, 1988; van der Krol et al., Biotechniques (1988) 6:958-976); co-suppression (Napoli, et al, Plant Cell 2:279-289, 1990); ribozymes (PCT Publication WO 97/10328); and combinations of sense and antisense (Waterhouse, et al., Proc. Natl. Acad. Sci. USA 95:13959-13964, 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., Proc. Natl. Acad. Sci. USA (1988) 85:8805-8809), a partial cDNA sequence including fragments of 5' coding sequence, (Cannon et al., Plant Molec. Biol. (1990) 15:3947), or 3' non-coding sequences (Ch'ng et al., Proc. Natl. Acad. Sci. USA (1989) 86:10006-10010). Cosuppression techniques may use the entire cDNA sequence (Napoli et al., supra; van der Krol et al., The Plant Cell (1990) 2:291-299) or a partial cDNA sequence (Smith et al., Mol. Gen. Genetics (1990) 224:477-481).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, Arch Virol Suppl 15:189-201, 1999]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., Cur Opin Plant Biol. 2(2):96-103, 1999; Dangond F, Physiol Genomics (2000) 2:53-58; van Hal N L et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Oil Content Phenotype

The invention further provides a method of identifying plants that have mutations in endogenous HIO102 that confer altered oil content, and generating altered oil content progeny of these plants that are not genetically modified. In one method, called "TILLING" (for targeting induced local lesions in genomes), mutations are induced in the seed of a plant of interest, for example, using EMS treatment. The resulting plants are grown and self-fertilized, and the progeny are used to prepare DNA samples. HIO102-specific PCR is used to identify whether a mutated plant has a HIO102 mutation. Plants having HIO102 mutations may then be tested for altered oil content, or alternatively, plants my be tested for altered oil content, and then HIO102-specific PCR is used to determine whether a plant having altered oil content has a mutated HIO102 gene. TILLING can identify mutations that may alter the expression of specific genes or the activity of proteins encoded by these genes (see Colbert et al (2001) Plant Physiol 126:480-484; McCallum et al (2000) Nature Biotechnology 18:455-457).

In another method, a candidate gene/Quantitative Trait Locus (QTLs) approach can be used in a marker-assisted breeding program to identify alleles of or mutations in the HIO102 gene or orthologs of HIO102 that may confer altered oil content (see Bert et al., Theor Appl Genet. 2003 June;107(1):181-9; and Lionneton et al, Genome. 2002 December;45(6):1203-15). Thus, in a further aspect of the invention, a HIO102 nucleic acid is used to identify whether a plant having altered oil content has a mutation in endogenous HIO102 or has a particular allele that causes altered oil content.

All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

Generation of Plants with a HIO102 Phenotype by Transformation with an Activation Tagging Construct Mutants were generated using the activation tagging "ACT-TAG" vector, pSKI015 (GI#6537289; Weigel D et al., supra). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacteriu*, Ti plasmid, an herbicide resistance selectable marker gene, and the 4×CaMV 35S enhancer element. Transgenic plants were selected at the T1 generation based on herbicide resistance.

T3 seed pools were analyzed by Near Infrared Spectroscopy (NIR), intact, at time of Harvest. NIR infrared spectra were captured using a Bruker 22 N/F. (See Narrative for experimental Detail). Bruker Software was used to estimate total seed oil, total seed protein, and total seed moisture content using data from NIR analysis and reference methods according to the manufacturers instructions. Oil contents predicted by our calibration (JL Oil Calib 2, Predicts GC determined oil) were compared for 15,720 individual T3 ACTTAG seed pools. The average NIR predicted oil content was 31.2%. Average NIR Predicted Protein was 20.4% and NIR Predicted Moisture was 6.4%. To identify high oil lines with normal protein content lines were identified that had an oil content of >34.5% and a normal protein content (>20%). These lines were evaluated for lines that also had normal or low moisture content. (<7%). Lines meeting these criteria were examined to identify lines with successful FST placements. Candidate genes near FST placements were evaluated based on their possible involvement in fatty acid biosynthesis or the biosynthesis of triacylglycerol. One line, IN023338 had high oil, normal protein and low moisture, as well as an ACTTAG insertion proximal to a gene that is similar in sequence to a known gene FAE1 (GI#18418411:1-1482; At4g34250), which is required for the elongation of C18 fatty acids to C20 and longer fatty acids in *Arabidopsis*. Although FAE1 is directly implicated in the production of long chain fatty acids (which account for about 20% of the fatty acids in *Arabidopsis* oil, the enzyme catalyzes a condensation reaction, which is required for the production of fatty acids of any length, not only long chain fatty acids.

Fatty acid content and quality were examined in IN023338 by standard GC methodology. GC analysis confirmed high oil content in the IN0233338 line but there was no significant difference in oil quality. Based on this, we concluded that altered expression of the FAE-like gene in IN023338 can confer increased oil content, and that the mechanism of action of this increase in oil content is distinct from the fatty acid profile changes that result from altered expression of the original FAE1 gene product, because oil content is increased in this line without a significant increase in the long chain fatty acid components of the seed oil. Altered expression of the FAE1-like gene could be accomplished by activation tagging, or by intentional alteration of expression under the control of appropriate promoter sequences or by other methods available in the art.

Example 2

Characterization of the T-DNA Insertion in Plants Exhibiting the Altered Oil Content Phenotype.

We performed standard molecular analyses, essentially as described in patent application PCT WO0183697, to determine the site of the T-DNA insertion associated with the altered oil content phenotype. Briefly, genomic DNA was extracted from plants exhibiting the altered oil content phenotype. PCR, using primers specific to the pSKI015 vector, confirmed the presence of the 35S enhancer in plants from lines IN0232577 and IN022173, and Southern blot analysis verified the genomic integration of the ACTTAG T-DNA and showed the presence of single T-DNA insertions in each of the transgenic lines.

Inverse PCR was used to recover genomic DNA flanking the T-DNA insertion, which was then subjected to sequence analysis using a basic BLASTN search and/or a search of the *Arabidopsis* Information Resource (TAIR) database (available at the arabidopsis.org website). It was determined that the left border junction was located at about nucleotide 43,605 of chromosome 4 (GI#7270366). About 3.2 kb upstream of the predicted right border is gene At4g34250 encoding fatty acid elongase at nucleotides 40,446-41,927.

Example 3

Analysis of *Arabidopsis* HIO102 Sequence

Sequence analyses were performed with BLAST (Altschul et al., 1997, J. Mol. Biol. 215:403-410), PFAM (Bateman et al., 1999, Nucleic Acids Res 27:260-262), PSORT (Nakai K, and Horton P, 1999,Trends Biochem Sci 24:34-6), and/or CLUSTAL (Thompson J D et al, 1994, Nucleic Acids Res 22:4673-4680).

The following eight *Arabidopsis* ESTs exactly match candidate gene At4g34250: GI nos 19876922, 498541, 9782785, 9788661, 9784101, 9785025, 9786448, and 506598. Five ESTs are from developing seeds (5 to 13 DAF) and two are in 5d-old etiolated seedlings, indicating that At4g34250 is largely seed specific and expressed during both early and late developmental stages. There is 1 EST from "dark grown" tissue, which may include seedlings.

BLASTN also identified a set of *Arabidopsis* genes & *Brassica* FAE1-like homologs. ClustalW analysis of these sequences indicates that a group of fatty-acid-elongase-like genes form 3 clades, two of which contain a functionally characterized gene (only Atg43760 occurs as an outgroup). These clades are supported by a cluster analysis of the amino acid sequences deduced from these genes as well.

Clade 1 includes the candidate gene At4g34250 and At2g15090, another putative fatty acid elongase. These two genes are 83% identical at the nucleotide level, and they could be inferred to have similar functions. It is significant that these two *Arabidopsis* genes cluster separately from the FAE1 and CUT1 clades. This would seem to indicate that their activity may be similar to the other groups (fatty acid synthesis), but may also differ in an important way, such as in the enzyme's substrate specificity.

Clade 2 includes *Arabidopsis* FAE1 & L. fendleri KCS3. Both gene products elongate 18:1 to 20:1 in seeds. The five *Brassica* KCS genes also fall into this clade.

Clade 3 includes CUT1 (an epidermis-specific very-long-chain fatty acid condensing enzyme involved in wax biosynthesis), At4g34510 (the gene adjacent to FAE1 on chromosome 4) & At2g16280 (a putative beta-ketoacyl-CoA synthase).

Candidate gene At4g34250 is 83% identical to a second *Arabidopsis* gene predicted to encode a fatty acid elongase, At2g15090 (gi|18397720).

Other putative orthologs identified by BLASTN include: Lesquerella fendleri 3-ketoacyl-CoA synthase (KCS3) gene, gi|4423334; *Brassica napus* 3-ketoacyl-CoA synthase gene, gi|19919737; *Brassica rapa* 3-ketoacyl-CoA synthase gene, gi|19919735; *Brassica oleracea* 3-ketoacyl-CoA synthase gene, gi|19919733; *Brassica napus* 3-ketoacyl-CoA synthase gene, gi|19919731; *Brassica napus* beta-ketoacyl-CoA synthase (FAE1.1), gi|14495234; *Arabidopsis thaliana* putative ketoacyl-CoA synthase, gi|18418463 (At4g34510); *Arabidopsis thaliana* putative beta-ketoacyl-CoA synthase, gi|18398069 (At2g16280), *Arabidopsis thaliana* very-long-chain fatty acid condensing enzyme CUT1, gi|18394739 (At1g19440); *Arabidopsis thaliana* putative beta-ketoacyl-CoA synthase, gi|14334713 (At5g43760); and *Arabidopsis thaliana* fatty acid elongase 1, gl|18418464 (At4g34520).

Additionally, soybean and cotton ESTs were identified that contig into 3 additional putative ortholog encoding genes as set forth in SEQ ID NOs: 3-5. Specifically, SEQ ID NO:3 is a contig of soybean ESTs having GI#s 8825889, 8825881, 10253399, and 10235530; SEQ ID NO:4 is a contig of soybean ESTs having GI#s 14258911, 13790811, 6455633, 6847127, 4313778, and 6847677; and SEQ ID NO:5 is a contig of cotton ESTs having GI#s 21100924, 21100866, 12200119, 21098784, 21098552, 21095047, 21095036, 21090830, 13354045, and 13350225.

BLASTP analysis identified the following putative orthologs: *Arabidopsis* putative fatty acid elongase, gi|15226055 (At2g15090); and fatty acid elongase 1 GI|15236144 (At4g34520).

Residues 175-279 of SEQ ID NO:2 show homology to a motif in the NCBI Conserved Domain Database (CDD); gnl|CDD|5947, pfam00195, Chal_stil_synt, Chalcone and stilbene synthases, N-terminal domain. The C-terminal domain of Chalcone synthase is reported to be structurally similar to domains in thiolase and beta-ketoacyl synthase. The differences in activity are accounted for by differences in this N-terminal domain.

Residues 387 to 454 are similar to gnl|CDD|3304, pfam02797, Chal_stil_syntC, Chalcone and stilbene synthases, C-terminal domain. This domain of chalcone synthase is reported to be structurally similar to domains in thiolase and beta-ketoacyl synthase. The differences in activity are accounted for by differences in the N-terminal domain.

These protein motifs are consistent with expectations for a fatty acid elongase. Fatty acid elongase enzymes (such as the biochemically characterized FAE1) may be cytosolic and are membrane localized. They are believed to occur as part of a complex of 4 enzymatic activities, including the 3-ketoacyl-CoA synthase (elongase), 3-ketoacyl-CoA reductase, 3-hydroxyacyl-CoA dehydrase and enoyl-CoA reductase. The elongase may help define the substrate specificity of the overall reaction. The other components of this complex remain largely uncharacterized.

Based on the computational data, the candidate gene product is predicted to function as a fatty acid condensing enzyme. It is predicted to be expressed primarily in developing seeds and changes in its expression in the mutants contributes to the observed high seed oil phenotype.

It is claimed:

1. A method of producing oil comprising:
   a) introducing into progenitor cells of a plant a heterologous constitutive promoter operatively linked to a heterologous polynucleotide that encodes a HIO102 polypeptide comprising an amino acid sequence having at least 95% sequence identity to the amino acid sequence of SEQ ID NO:2, wherein the polypeptide confers a high oil phenotype of increased oil content relative to a plant of the same species not comprising the heterologous constitutive promoter operatively linked to the heterologous polynucleotide, and wherein there is no statistically significant increase in the proportion of long chain fatty acid components of seed oil relative to seed oil from a plant of the same species not comprising the heterologous constitutive promoter operatively linked to the heterologous polynucleotide;
   b) growing the transformed progenitor cells to produce a transgenic plant, wherein said heterologous polynucleotide sequence is expressed;
   c) identifying a transgenic plant that exhibits the high oil content phenotype; and
   d) recovering oil from said transgenic plant.

2. The method of claim 1, wherein the plant is selected from the group consisting of rapeseed, soy, corn, sunflower, cotton, cocoa, safflower, oil palm, coconut palm, flax, castor and peanut.

3. A method of producing a plant with a high oil phenotype, said method comprising:
   a) introducing into progenitor cells of the plant a heterologous constitutive promoter operatively linked to a heterologous polynucleotide that encodes a HIO102 polypeptide comprising an amino acid sequence having at least 95% sequence identity to the amino acid sequence of SEQ ID NO:2, wherein the polypeptide confers a high oil phenotype of increased oil content relative to a plant of the same species not comprising the heterologous constitutive promoter operatively linked to the heterologous polynucleotide, and wherein there is no statistically significant increase in the proportion of long chain fatty acid components of seed oil relative to seed oil from a plant of the same species not comprising the heterologous constitutive promoter operatively linked to the heterologous polynucleotide;
   b) growing the transformed progenitor cells to produce a transgenic plant, wherein said heterologous polynucleotide sequence is expressed; and
   c) identifying a transgenic plant that exhibits the high oil content phenotype.

4. The method of claim 3, wherein the plant is selected from the group consisting of rapeseed, soy, corn, sunflower, cotton, cocoa, safflower, oil palm, coconut palm, flax, castor and peanut.

* * * * *

UNITED STATES PATENT AND TRADEMARK OFFICE
CERTIFICATE OF CORRECTION

PATENT NO.        : 7,750,205 B2
APPLICATION NO. : 10/539488
DATED             : July 6, 2010
INVENTOR(S)       : Lightner et al.

It is certified that error appears in the above-identified patent and that said Letters Patent is hereby corrected as shown below:

On the Cover:

Page 2, Under OTHER PUBLICATIONS, (1st Column, Line 3), "13-Ketoacyl-CoA" should be --β-Ketoacyl-CoA--.

In the Specification:

Column 2, Line 18, "(axmieux" should be --(Lemieux--.

Column 2, Line 58, "Pridborg" should be --Fridborg--.

Column 8, Line 41, "fornmaride" should be --formamide--.

Column 11, Line 17, "se Block" should be --(De Block--.

Column 15, Line 55, "gi|4423334" should be --gi|14423334--.

Signed and Sealed this

Fifth Day of October, 2010

David J. Kappos
*Director of the United States Patent and Trademark Office*

SEQUENCE LISTING

<160> NUMBER OF SEQ ID NOS: 5

<210> SEQ ID NO 1
<211> LENGTH: 1482
<212> TYPE: DNA
<213> ORGANISM: Arabidopsis thaliana

<400> SEQUENCE: 1

```
atggattacc ccatgaagaa ggtaaaaatc tttttcaact acctcatggc gcatcgcttc      60
aagctctgct tcttaccatt aatggttgct atagccgtgg aggcgtctcg tctttccaca     120
caagatctcc aaaactttta cctctactta caaaacaacc acacatctct aaccatgttc     180
ttcctttacc tcgctctcgg tcgactctt tacctcatga cccggcccaa acccgtttat     240
ctcgttgact ttagctgcta cctcccaccg tcgcatctca aagccagcac ccagaggatc     300
atgcaacacg taaggcttgt acgagaagca ggcgcgtgga agcaagagtc cgattacttg     360
atggacttct gcgagaagat tctagaacgt tccggtctag gccaagagac gtacgtaccc     420
gaaggtcttc aaactttgcc actacaacag aatttggctg tatcacgtat agagacggag     480
gaagttatta ttggtgcggt cgataatctg tttcgcaaca cgggaataag ccctagtgat     540
ataggtatat tggtggtgaa ttcaagcact tttaatccaa caccttcgct atcaagtatc     600
ttagtgaata agtttaaact tagggataat ataaagagct tgaatcttgg tgggatgggg     660
tgtagcgctg gagtcatcgc tatcgatgcg gctaagagct tgttacaagt tcatagaaac     720
acttatgctc ttgtggtgag cacggagaac atcactcaaa acttgtacat gggtaacaac     780
aaatcaatgt tggttacaaa ctgtttgttc cgtataggtg gggccgcgat tttgcttttct    840
aaccggtcta tagatcgtaa acgcgcaaaa tacgagcttg ttcacaccgt gcgggtccat     900
accggagcag atgaccgatc ctatgaatgt gcaactcaag aagaggatga agatggcata     960
gttggggttt ccttgtcaaa gaatctacca atggtagctg caagaaccct aaagatcaat    1020
atcgcaactt tgggtccgct tgttcttccc ataagcgaga gtttcacttt ctttgtgagg    1080
ttcgttaaaa agaagtttct caaccccaag ctaaagcatt acattccgga tttcaagctc    1140
gcattcgagc atttctgtat ccatgcgggt ggtagagcgc taattgatga atggagaag     1200
aatcttcatc taactccact agacgttgag gcttcaagaa tgacattaca caggtttggt    1260
aatacctctt cgagctccat ttggtacgag ttggcttaca cagaagccaa aggaaggatg    1320
acgaaaggag ataggatttg gcagattgcg ttggggtcag gttttaagtg taatagttca    1380
gtttgggtgg ctcttcgtaa cgtcaagcct tctactaata atccttggga acagtgtcta    1440
cacaaatatc cagttgagat cgatatagat ttaaaagagt ga                       1482
```

<210> SEQ ID NO 2
<211> LENGTH: 493
<212> TYPE: PRT
<213> ORGANISM: Arabidopsis thaliana

<400> SEQUENCE: 2

```
Met Asp Tyr Pro Met Lys Lys Val Lys Ile Phe Phe Asn Tyr Leu Met
1               5                   10                  15

Ala His Arg Phe Lys Leu Cys Phe Leu Pro Leu Met Val Ala Ile Ala
            20                  25                  30

Val Glu Ala Ser Arg Leu Ser Thr Gln Asp Leu Gln Asn Phe Tyr Leu
        35                  40                  45

Tyr Leu Gln Asn Asn His Thr Ser Leu Thr Met Phe Phe Leu Tyr Leu
    50                  55                  60

Ala Leu Gly Ser Thr Leu Tyr Leu Met Thr Arg Pro Lys Pro Val Tyr
65                  70                  75                  80

Leu Val Asp Phe Ser Cys Tyr Leu Pro Pro Ser His Leu Lys Ala Ser
                85                  90                  95
```

```
Thr Gln Arg Ile Met Gln His Val Arg Leu Val Arg Glu Ala Gly Ala
            100                 105                 110

Trp Lys Gln Glu Ser Asp Tyr Leu Met Asp Phe Cys Glu Lys Ile Leu
        115                 120                 125

Glu Arg Ser Gly Leu Gly Gln Glu Thr Tyr Val Pro Glu Gly Leu Gln
    130                 135                 140

Thr Leu Pro Leu Gln Gln Asn Leu Ala Val Ser Arg Ile Glu Thr Glu
145                 150                 155                 160

Glu Val Ile Ile Gly Ala Val Asp Asn Leu Phe Arg Asn Thr Gly Ile
                165                 170                 175

Ser Pro Ser Asp Ile Gly Ile Leu Val Val Asn Ser Ser Thr Phe Asn
            180                 185                 190

Pro Thr Pro Ser Leu Ser Ser Ile Leu Val Asn Lys Phe Lys Leu Arg
        195                 200                 205

Asp Asn Ile Lys Ser Leu Asn Leu Gly Gly Met Gly Cys Ser Ala Gly
    210                 215                 220

Val Ile Ala Ile Asp Ala Ala Lys Ser Leu Leu Gln Val His Arg Asn
225                 230                 235                 240

Thr Tyr Ala Leu Val Val Ser Thr Glu Asn Ile Thr Gln Asn Leu Tyr
                245                 250                 255

Met Gly Asn Asn Lys Ser Met Leu Val Thr Asn Cys Leu Phe Arg Ile
            260                 265                 270

Gly Gly Ala Ala Ile Leu Leu Ser Asn Arg Ser Ile Asp Arg Lys Arg
        275                 280                 285

Ala Lys Tyr Glu Leu Val His Thr Val Arg Val His Thr Gly Ala Asp
    290                 295                 300

Asp Arg Ser Tyr Glu Cys Ala Thr Gln Glu Glu Asp Glu Asp Gly Ile
305                 310                 315                 320

Val Gly Val Ser Leu Ser Lys Asn Leu Pro Met Val Ala Ala Arg Thr
                325                 330                 335

Leu Lys Ile Asn Ile Ala Thr Leu Gly Pro Leu Val Leu Pro Ile Ser
            340                 345                 350

Glu Lys Phe His Phe Phe Val Arg Phe Val Lys Lys Phe Leu Asn
        355                 360                 365

Pro Lys Leu Lys His Tyr Ile Pro Asp Phe Lys Leu Ala Phe Glu His
    370                 375                 380

Phe Cys Ile His Ala Gly Gly Arg Ala Leu Ile Asp Glu Met Glu Lys
385                 390                 395                 400

Asn Leu His Leu Thr Pro Leu Asp Val Glu Ala Ser Arg Met Thr Leu
                405                 410                 415

His Arg Phe Gly Asn Thr Ser Ser Ser Ile Trp Tyr Glu Leu Ala
            420                 425                 430

Tyr Thr Glu Ala Lys Gly Arg Met Thr Lys Gly Asp Arg Ile Trp Gln
        435                 440                 445

Ile Ala Leu Gly Ser Gly Phe Lys Cys Asn Ser Ser Val Trp Val Ala
    450                 455                 460

Leu Arg Asn Val Lys Pro Ser Thr Asn Asn Pro Trp Glu Gln Cys Leu
465                 470                 475                 480

His Lys Tyr Pro Val Glu Ile Asp Ile Asp Leu Lys Glu
                485                 490
```

<210> SEQ ID NO 3
<211> LENGTH: 657
<212> TYPE: DNA

```
<213> ORGANISM: Glycine max
<220> FEATURE:
<221> NAME/KEY: misc_feature
<222> LOCATION: (653)..(654)
<223> OTHER INFORMATION: n is a, c, g, or t

<400> SEQUENCE: 3
ggaattcggc acgaggcaag tcctacggct gtgtcttcca agaagaagat gagacaaaaa        60
gaattggtgt ggcactctca aaagacctaa tggctgtggc aggagaggcc ctaaagacca       120
acatcacaac actaggaccc ttggtcctcc ctatgtcaga acagcttctt ttctttgcca       180
cattggtggc taggaaagtg ttcaagatga agataaaacc atacatccca gatttcaagt       240
tggcctttga gcattttttgc attcatgctg agggagggc agtgttggat gagttggaga       300
agaatcttga gctctctgat ggcacatgg agccctcaag gatgacacta aataggtttg       360
gtaacacttc tagcagttcc ttgtggtatg aattggccta cactgaagcc aaagggagga       420
tcaagaaagg tgacaggact tggcagattg catttgggtc agggtttaag tgcaacagtg       480
ctgtgtggag ggctttgagg accatcaatc ctgctaagga gaacaatcct tggatggatg       540
agattcatga ctttccagtt catgtgccta agtggcacc aattgcttcc taaattaatc       600
aaacatcttt ttctctttt agtatgattc taaaattaaa gaaacttgtt cannaac           657

<210> SEQ ID NO 4
<211> LENGTH: 1130
<212> TYPE: DNA
<213> ORGANISM: Glycine max

<400> SEQUENCE: 4
aacattactc agaattggta ctttgggaac aagaaatcca tgctcattcc caattgccta        60
tttcgtgtgg gctgctctgc gctgcttctc tctaacaagc cggcagatcg aaggagggcc       120
aagtaccggc ttgtccacgt cgtgaggact catcgcgggg ccgacgacaa ggcgttccgg       180
tgtgtttacc aggagcagga tgatgctggg aaaactggtg tttccttgtc taaggatttg       240
atggcaattg ctggtggagc attgaagact aacatcacca cacttggtcc tctggtgctg       300
ccaattagtg agcagcttct gttttttcgtg actctgctga tgaacaagtt atttaaggct       360
ggtgtgaagc cttacatacc ggatttcaag cttgcatttg atcatttttg tatccatgct       420
ggtggcaggg ctgtgattga tgagttggag aagaacctgc agctgcttcc tgagcatgtg       480
gaggcttcta ggatgacccct tcatagattt gggaacactt cctcaagctc catttggtat       540
gagttggctt acattgaagc caaagggagg atcaagaagg gtaacaggat ttggcaaatt       600
gcgtttggaa gtggttcaa gtgtaacagt gcggtttggc aggctctgag gaatgtgagg       660
ccttctccta atggaccatg ggaagattgc attcataagt atcctgtgga aatagtcaca       720
tagtgatcat agttcagttc agttctcagt cacatactct ggctgctaca acttaattca       780 gggtacccctt cattagtttc cagatccatt gtctctctct ctgttgtaga tttcattgtg       840
taattcactg cctctttttgt gtttgatgat tgtggattt cattgggtta aattcatgta       900
tctggagtaa tatgatatgg ggaattcctg aattttttt cttcctgctg atgcacttat       960
gaatttttat ttttttagtc ataaagttgc gcctgggtaa cgaggcgctt ataggccccg      1020
atgcgaaaat actcctttga catatgtagg ggtgacggta ccactgccca ataattctct      1080
cccatatttt tacgcaacga ggacccttta gcctcgcgga ccagagctgc                 1130

<210> SEQ ID NO 5
<211> LENGTH: 960
```

-continued

```
<212> TYPE: DNA
<213> ORGANISM: Gossypium arboreum

<400> SEQUENCE: 5
tggagaacat tactctcaac tgggacttcg gcaacgaccg atccatgcta gtctctaact      60
gcttgttccg tatgggcggt gccgcgatcc ttctatcaaa ccggtcatcc gatcgccgcc     120
gctccaagta ccaactcatc cacaccgtac gaacccacaa aggagccgac gacaaatgct     180
acaactgcgt cttccaacgt gaggacgaca ccaaacgaat aggcgtttcc ctctccaaag     240
acctcatggc ggtcgccggc gaagccctca aaccaacat caccaccctc ggtccattag      300
tcctccccat gtccgaacaa ctcctctttt tcatcactt agtagcccga aaagtcttca      360
aaatgaagat caggccatac atcccggatt tcaaactagc tttcgagcat ttttgcatcc     420
atgcaggtgg gagagccgtg ttagatgagc tagaaaagaa ccttgagctc tcagattggc     480
acatggaacc atcgaggatg acactttaca ggttcggtaa cacgtcgagc agctctttat     540
ggtacgaact agcttactcg gaagccaaag gaaggatccg aaaaggtgat cggacatggc     600
agattgcatt cgggtcaggg tttaaatgca acagtgctgt atggaaagca ttgaagacca     660
ttaatccagc aaaggagaag agtccatgga ttgatgaaat tgatgaatat cctgtttatg     720
tgcctaaggt ggccactgtt tcttcttctt cttcttccca aaaaaccata taattttcat     780
cattcaaagg aagagaatag agagaaagag aggacttaat cagtaattat tagaactatg     840
atttattttt tattttttta catgtttaat tgtgtgttga tttgaagatt aatttattcc     900
aagttgaaga tatatatata taattttctt ttcatttgca aaaaaaaaa aagaaactcg      960
```